(12) United States Patent
Cowperthwait et al.

(10) Patent No.: US 12,274,447 B1
(45) Date of Patent: Apr. 15, 2025

(54) ILLUMINATION SYSTEMS FOR SURGICAL STAPLERS

(71) Applicant: CILAG GMBH INTERNATIONAL, Zug (CH)

(72) Inventors: Matthew D. Cowperthwait, Cincinnati, OH (US); Christopher Denzinger, Cincinnati, OH (US); Shane R. Adams, Lebanon, OH (US); Eric Lafay, Cincinnati, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 0 days.

(21) Appl. No.: 18/394,931

(22) Filed: Dec. 22, 2023

(51) Int. Cl.
*A61B 90/30* (2016.01)
*A61B 17/115* (2006.01)

(52) U.S. Cl.
CPC .......... *A61B 17/1155* (2013.01); *A61B 90/30* (2016.02)

(58) Field of Classification Search
CPC ..................... A61B 17/1155; A61B 90/30
See application file for complete search history.

(56) References Cited

U.S. PATENT DOCUMENTS

| 7,918,377 | B2 | 4/2011 | Measamer |
| 9,757,133 | B2* | 9/2017 | Latimer ............... A61B 17/064 |
| 2021/0346026 | A1* | 11/2021 | Valentine ............... A61B 90/30 |
| 2022/0015856 | A1 | 1/2022 | Vadali |

* cited by examiner

*Primary Examiner* — Nathaniel C Chukwurah
(74) *Attorney, Agent, or Firm* — TROUTMAN PEPPER LOCKE LLP

(57) ABSTRACT

The present disclosure provides a stapling apparatus. The apparatus includes a trocar, a stapling head assembly, and an anvil. The stapling head assembly includes one or more lights positioned on a surface of a tubular casing of the stapling head assembly, the lights extending parallel to a longitudinal axis of the stapling head assembly. The row of lights provide an illumination system to provide indicators of device orientation or location.

20 Claims, 12 Drawing Sheets

ILLUMINATION SYSTEMS FOR SURGICAL STAPLERS

FIELD OF THE INVENTION

The present disclosure describes surgical instruments with illumination systems for locating the instrument within a patient during a surgical procedure.

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis. The end-to-end anastomosis may provide a substantially unobstructed flow path from one portion of the digestive tract to the other portion of the digestive tract, without also providing any kind of leaking at the site of the anastomosis.

One example of an instrument that may be used to provide an end-to-end anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice. In situations wherein the stapler is inserted into the patient's abdomen or covering tissue, it can be difficult to locate a transition between the proximal portions of the stapler (i.e., the handle portion) and the distal portions (i.e., the anvil portion).

BACKGROUND

The present disclosure provides solutions to the needs mentioned above. One aspect of the present disclosure provides an apparatus. The apparatus includes a trocar. The apparatus includes a stapling head assembly. The stapling head assembly includes a deck surface, a tubular casing, an array of staple openings formed through the deck surface, and a plurality of staples associated with the array of staple openings, wherein the stapling head assembly is operable to drive the staples through the array of staple openings. The stapling head assembly further includes a first longitudinal row of lights positioned on a surface of the tubular casing and extending parallel to a longitudinal axis of the stapling head assembly. The apparatus includes an anvil including an anvil surface configured to compress tissue against the deck surface, wherein the anvil surface defines an array of staple forming pockets. The anvil further includes an anvil shank extending along an anvil longitudinal axis, wherein the anvil shank is configured to couple with one of the stapling head assembly and the trocar.

The apparatus includes a trocar. The apparatus includes a stapling head assembly. The stapling head assembly includes a deck surface, a tubular casing, an array of staple openings formed through the deck surface, and a plurality of staples associated with the array of staple openings, wherein the stapling head assembly is operable to drive the staples through the array of staple openings. The stapling head assembly further includes a plurality of distal staple lights positioned around the deck surface indicating a location of the deck surface during operation of the apparatus. The apparatus includes an anvil including an anvil surface configured to compress tissue against the deck surface, wherein the anvil surface defines an array of staple forming pockets. The anvil further includes an anvil shank extending along a longitudinal axis, wherein the anvil shank is configured to couple with one of the stapling head assembly and the trocar.

The apparatus includes a trocar. The apparatus includes a stapling head assembly. The stapling head assembly includes a deck surface, a tubular casing, an array of staple openings formed through the deck surface, and a plurality of staples associated with the array of staple openings, wherein the stapling head assembly is operable to drive the staples through the array of staple openings. The stapling head assembly further includes a distal staple light positioned around the deck surface indicating a location of the deck surface during operation of the apparatus. The stapling head assembly further includes a plurality of radial staple lights extending around a perimeter of the tubular casing. The apparatus includes an anvil including an anvil surface configured to compress tissue against the deck surface, wherein the anvil surface defines an array of staple forming pockets. The anvil further includes an anvil shank extending along a longitudinal axis, wherein the anvil shank is configured to couple with one of the stapling head assembly and the trocar.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
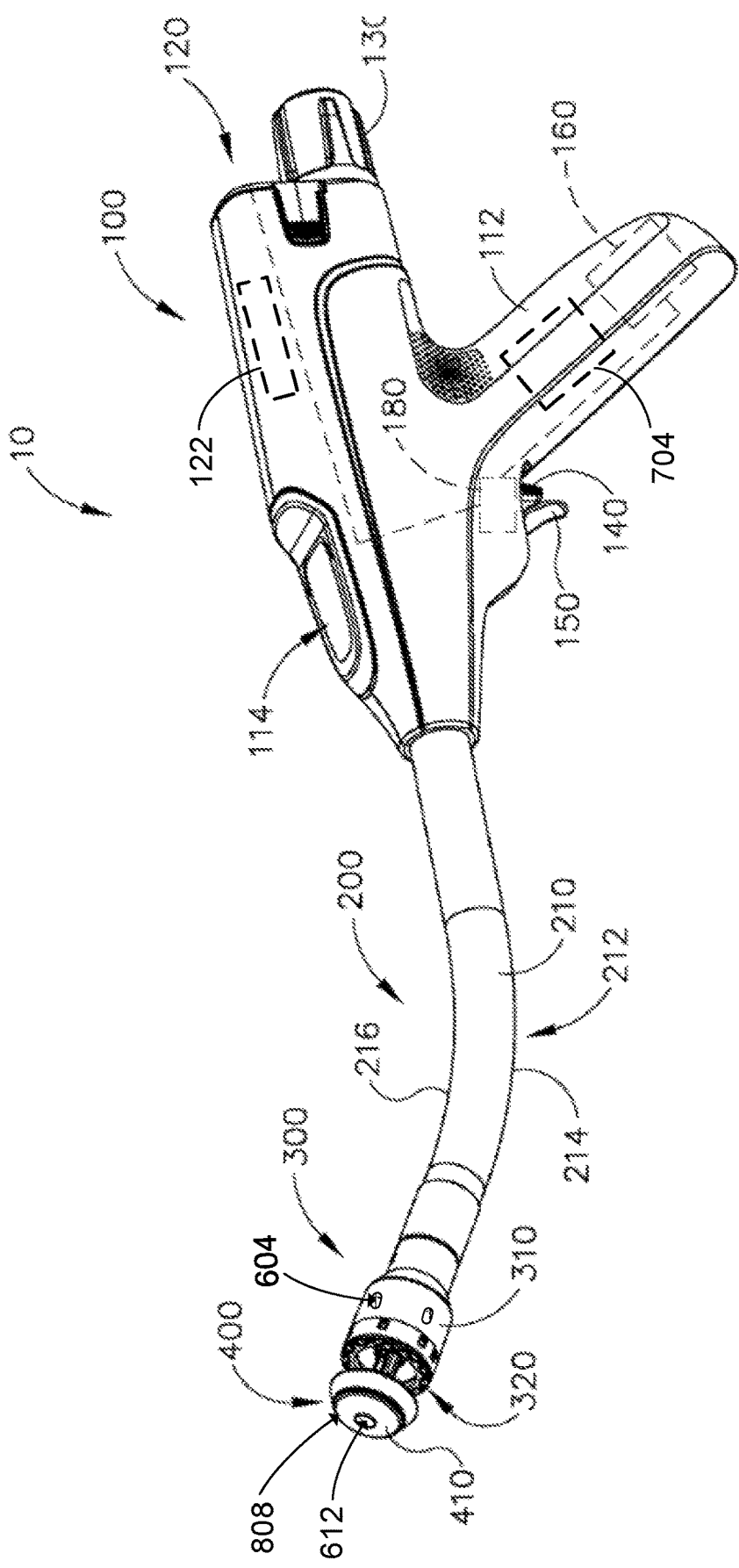
FIG. 1 depicts a perspective view of an exemplary circular stapler, according to one aspect of the present disclosure.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

Figure 2:
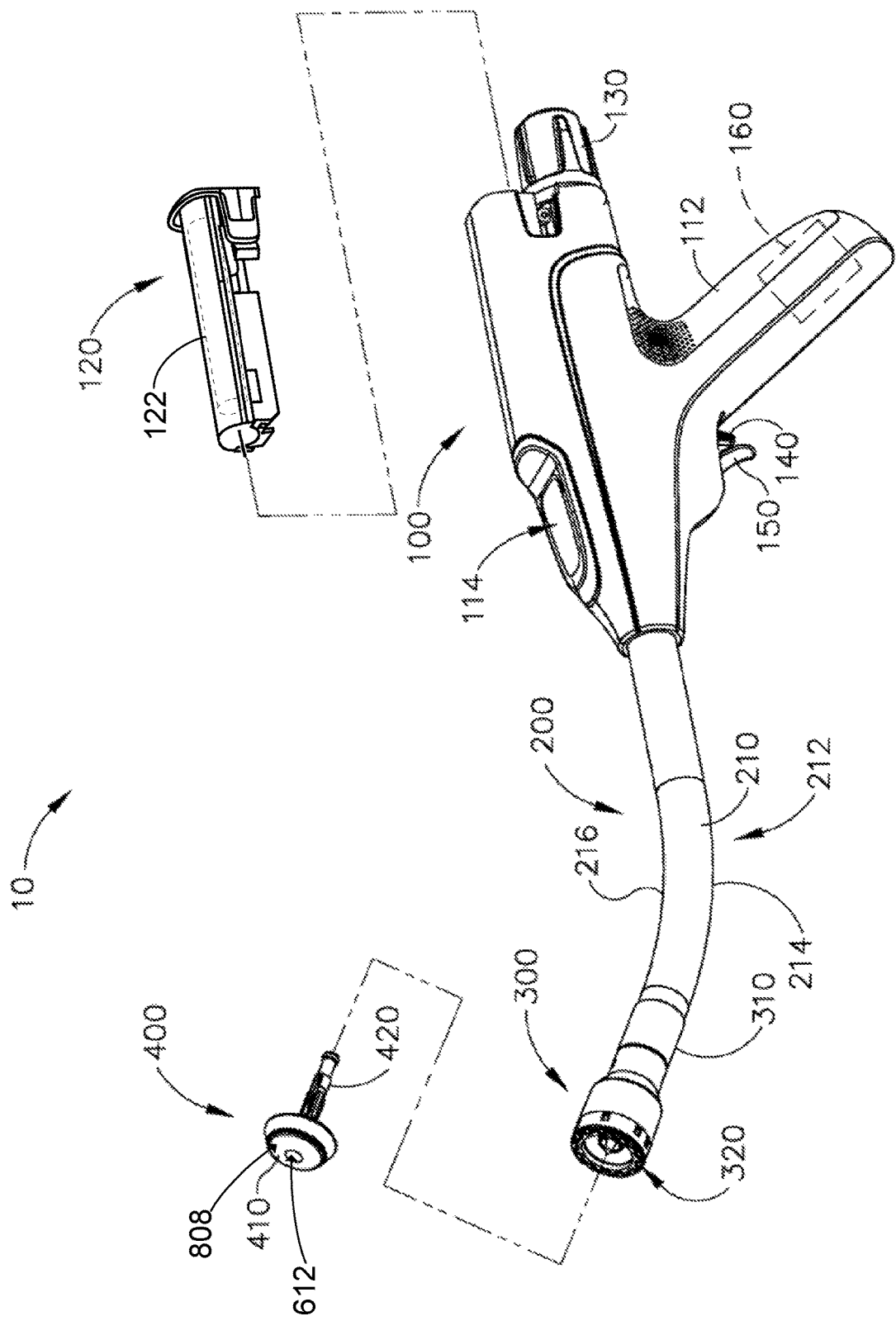
FIG. 2 depicts a perspective view of the circular stapler of FIG. 1, with a control attachment removed from a handle assembly and an anvil removed from a stapling head assembly, according to one aspect of the present disclosure.

FIGS. 1-2 depict an exemplary surgical circular stapling instrument (10) that may be used to provide an end-to-end anastomosis between two sections of an anatomical lumen such as a portion of a patient's digestive tract. Surgical stapler (10) of this example comprises a handle assembly (100), a shaft assembly (200), a stapling head assembly (300), an anvil (400), and a removable battery pack (120). Each of these components will be described in greater detail below. As will be appreciated, the surgical staplers (10) shown in the figures each show a circular stapler, which is in accordance with a preferred embodiment. That said, the disclosure herein is not so limited, and the features described herein can also apply to other surgical staplers, including for example linear staplers. FIG. 1 depicts a circular stapler with two separate radial staple lights (608), which is in accordance with an embodiment of the present disclosure. FIG. 2 depicts a circular stapler without staple lights proximate its end effector assembly (e.g., stapling head assembly 300 and anvil 400). As will be appreciated, however, the embodiments shown in FIGS. 1 and 2 can include any of the lighting systems or combinations of the lighting systems described herein, for example trocar light (602), radial staple lights (608), longitudinal rows of lights (606, 610), anvil light (612), and/or switch (702) and controller (704).

A. Exemplary Tissue Engagement Features of Circular Stapling Instrument

Figure 3:
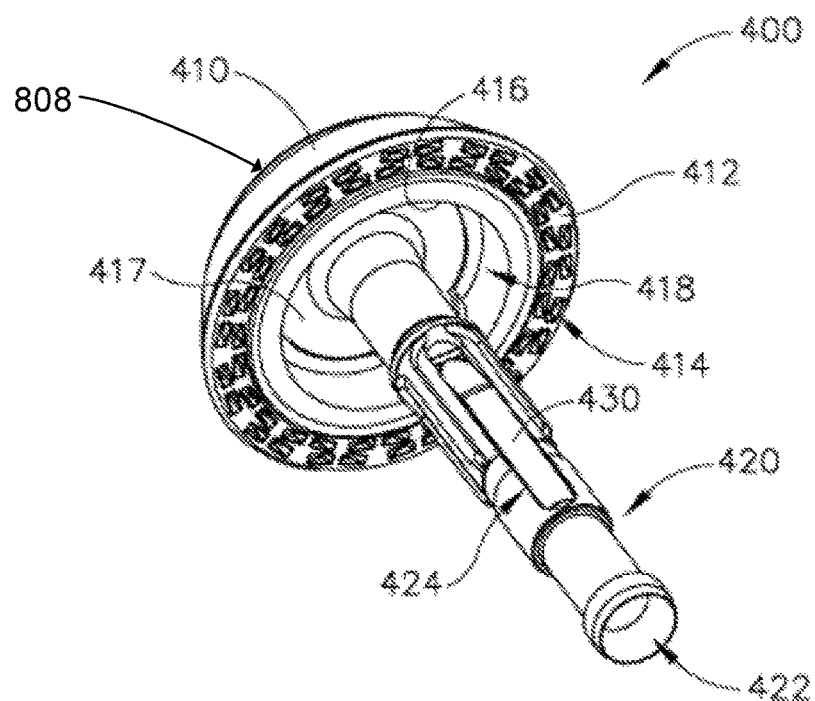
FIG. 3 depicts a perspective view of the anvil of the circular stapler of FIG. 1, according to one aspect of the present disclosure.

As best seen in FIG. 3, anvil (400) of the present example comprises a head (410) and a shank (420). Head (410) includes a proximal surface (412) that defines a plurality of staple forming pockets (414). Staple forming pockets (414) are arranged in two concentric annular arrays in the present example. Staple forming pockets (414) are configured to deform staples as the staples are driven into staple forming pockets (414) (e.g., deforming a generally "U" shaped staple into a "B" shape as is known in the art). Shank (420) defines a bore or lumen (422) and includes a pair of pivoting latch members (430) positioned in bore (422). Each latch member (430) includes features that allows anvil (400) to be removably secured to a trocar (330) of stapling head assembly (300) as will be described in greater detail below. It should be understood, however, that anvil (400) may be removably secured to a trocar (330) using any other suitable components, features, or techniques.

Figure 4:
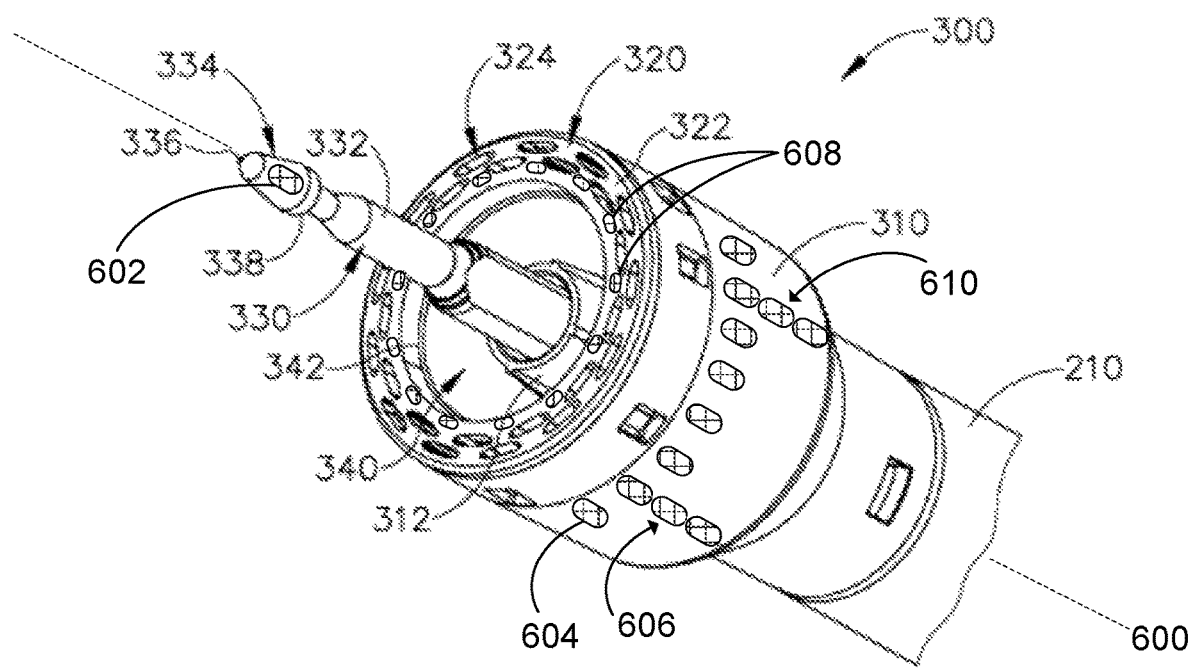
FIG. 4 depicts a perspective view of a stapling head assembly of a circular stapler with staple lights, according to one aspect of the present disclosure.
Figure 5:
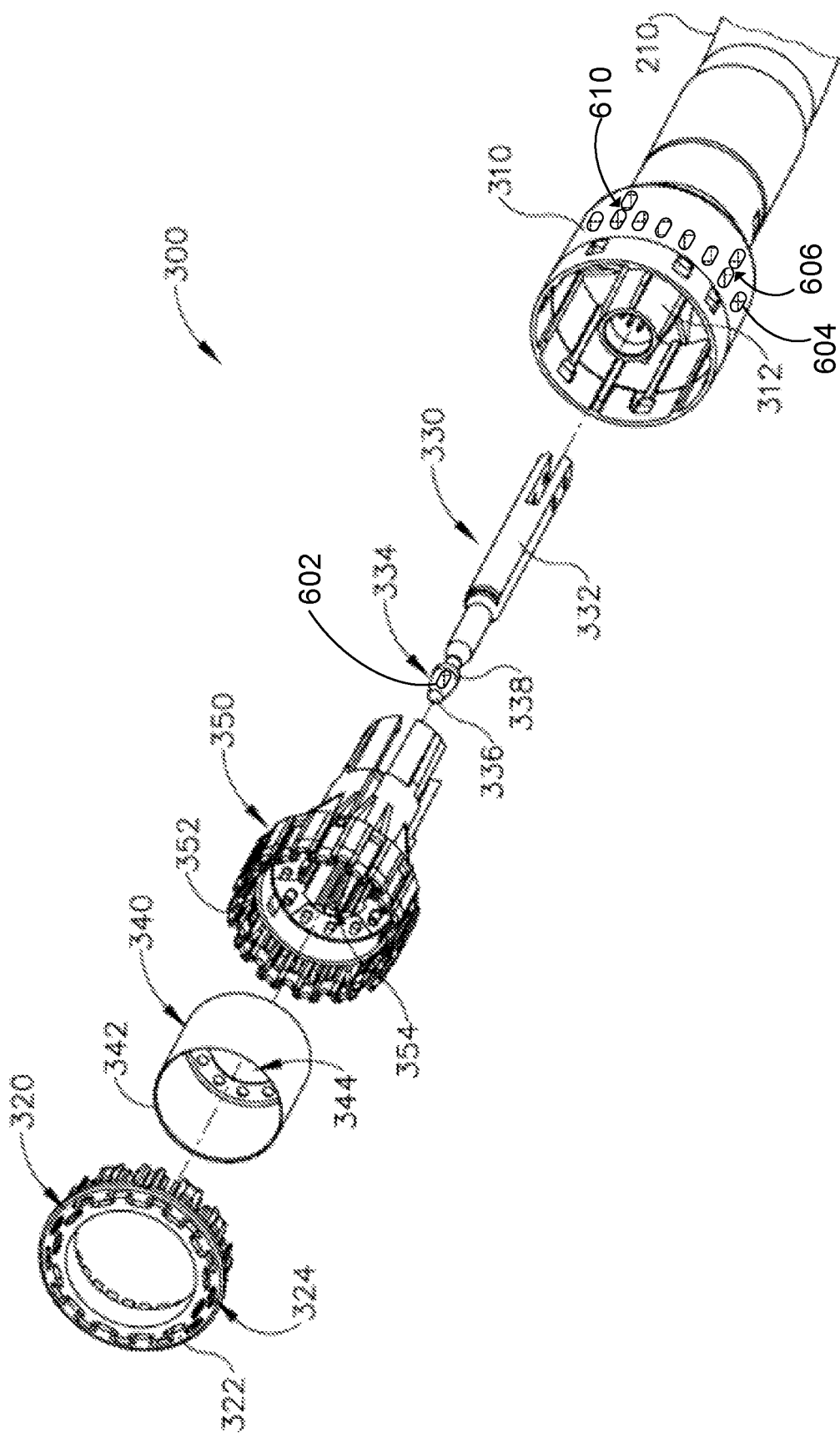
FIG. 5 depicts an exploded perspective view of the stapling head assembly of FIG. 4, according to one aspect of the present disclosure.

Stapling head assembly (300) is located at the distal end of shaft assembly (200). As shown in FIGS. 1-2, anvil (400) is configured to removably couple with shaft assembly (200), adjacent to stapling head assembly (300). As will be described in greater detail below, anvil (400) and stapling head assembly (300) are configured to cooperate to manipulate tissue in three ways, including clamping the tissue, cutting the tissue, and stapling the tissue. As best seen in FIGS. 4-5, stapling head assembly (300) of the present example comprises a tubular casing (310) housing a slidable staple driver member (350). A cylindraceous inner core member (312) extends distally within tubular casing (310). Tubular casing (310) is fixedly secured to an outer sheath (210) of shaft assembly (200), such that tubular casing (310) serves as a mechanical ground for stapling head assembly (300).

Trocar (330) is positioned coaxially within inner core member (312) of tubular casing (310). Trocar (330) is operable to translate distally and proximally relative to tubular casing (310) in response to rotation of a knob (130) located at the proximal end of handle assembly (100). Trocar (330) comprises a shaft (332) and a head (334). Head (334) includes a pointed tip (336) and an inwardly extending proximal surface (338). Head (334) and the distal portion of shaft (332) are configured for insertion in bore (422) of anvil (400). Proximal surface (338) is configured to complement features of latch members (430) to provide a snap fit between anvil (400) and trocar (330).

Staple driver member (350) is operable to actuate longitudinally within tubular casing (310) in response to activation of motor (160) as will be described in greater detail below. Staple driver member (350) includes two distally presented concentric annular arrays of staple drivers (352). Staple drivers (352) are arranged to correspond with the arrangement of staple forming pockets (414) described above. Thus, each staple driver (352) is configured to drive a corresponding staple into a corresponding staple forming pocket (414) when stapling head assembly (300) is actuated. Staple driver member (350) also defines a bore (354) that is configured to coaxially receive core member (312) of tubular casing (310).

A cylindraceous knife member (340) is coaxially positioned within staple driver member (350). Knife member (340) includes a distally presented, sharp circular cutting edge (342). Knife member (340) is sized such that knife member (340) defines an outer diameter that is smaller than the diameter defined by the inner annular array of staple drivers (352). Knife member (340) also defines an opening that is configured to coaxially receive core member (312) of tubular casing (310).

A deck member (320) is fixedly secured to tubular casing (310). Deck member (320) includes a distally presented deck surface (322) defining two concentric annular arrays of staple openings (324). Staple openings (324) are arranged to correspond with the arrangement of staple drivers (352) and staple forming pockets (414) described above. Thus, each staple opening (324) is configured to provide a path for a corresponding staple driver (352) to drive a corresponding staple through deck member (320) and into a corresponding staple forming pocket (414) when stapling head assembly (300) is actuated. It should be understood that the arrangement of staple openings (324) may be modified just like the arrangement of staple forming pockets (414) as described above. It should also be understood that various structures and techniques may be used to contain staples within stapling head assembly (300) before stapling head assembly (300) is actuated. Deck member (320) defines an inner diameter that is just slightly larger than the outer diameter defined by knife member (340). Deck member (320) is thus configured to allow knife member (340) to translate distally to a point where cutting edge (342) is distal to deck surface (322).

Figure 6:
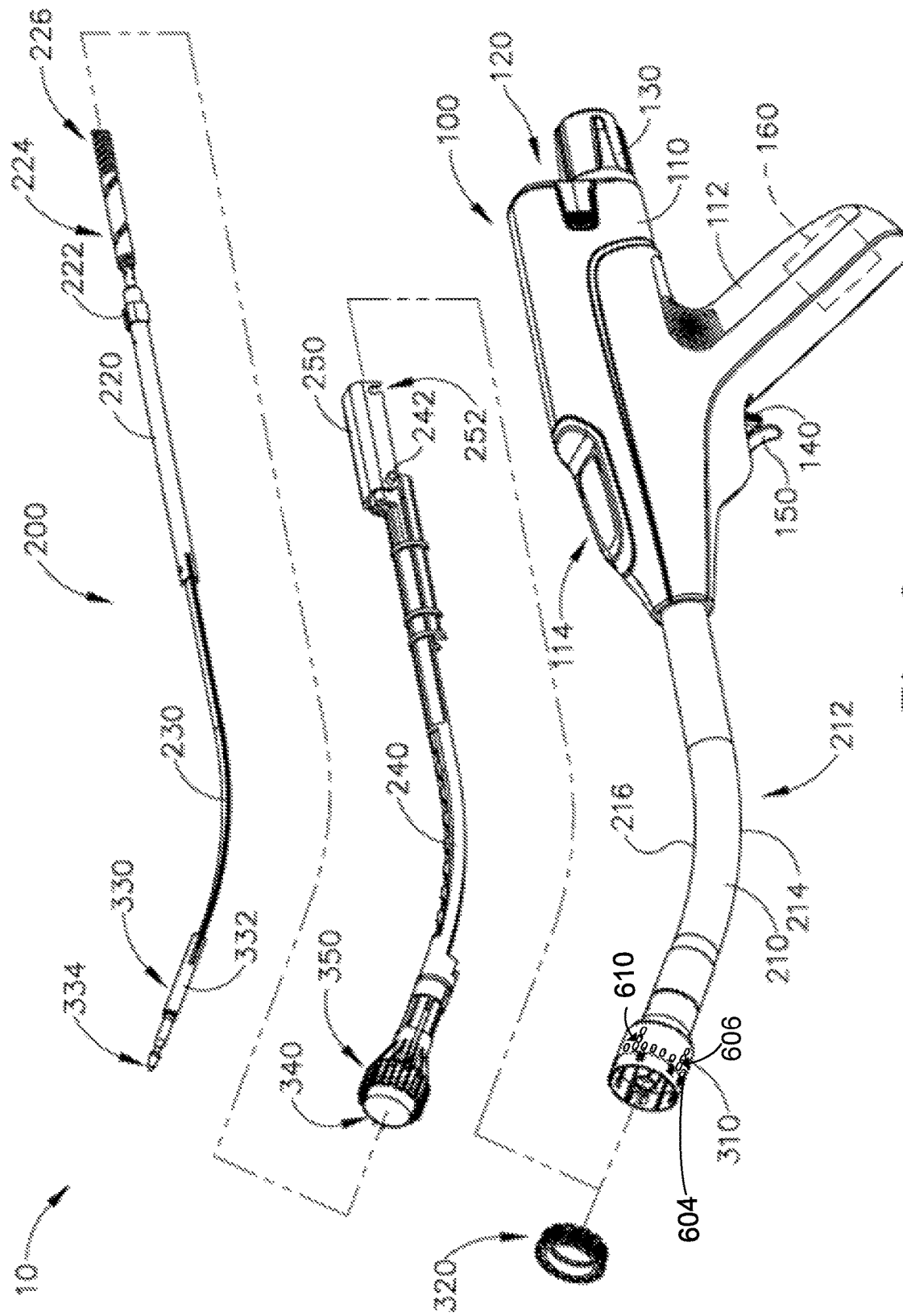
FIG. 6 depicts an exploded perspective view of the circular stapler defined in FIGS. 4 and 5, with portions of the shaft assembly shown separately from each other, according to one aspect of the present disclosure.

FIG. 6 shows various components of shaft assembly (200), which extends distally from handle assembly (100) and couples components of stapling head assembly (300) with components of handle assembly (100). In particular, and as noted above, shaft assembly (200) includes an outer sheath (210) that extends between handle assembly (100) and tubular casing (310). In the present example, outer sheath (210) is rigid and includes a preformed curved section (212) that is configured to facilitate positioning of stapling head assembly (300) within a patient's colon as described below. Curved section (212) includes an inner curve (216) and an outer curve (214).

Shaft assembly (200) further includes a trocar actuation rod (220) and a trocar actuation band assembly (230). The distal end of trocar actuation band assembly (230) is fixedly secured to the proximal end of trocar shaft (332). The proximal end of trocar actuation band assembly (230) is fixedly secured to the distal end of trocar actuation rod (220), such that trocar (330) will translate longitudinally relative to outer sheath (210) in response to translation of trocar actuation band assembly (230) and trocar actuation rod (220) relative to outer sheath (210). Trocar actuation band assembly (230) is configured to flex such that trocar actuation band assembly (230) may follow along the preformed curve in shaft assembly (200) as trocar actuation band assembly (230) is translated longitudinally relative to outer sheath (210). However, trocar actuation band assembly (230) has sufficient column strength and tensile strength to transfer distal and proximal forces from trocar actuation rod (220) to trocar shaft (332). Trocar actuation rod (220) is rigid. A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a coarse helical threading (224) and a fine helical threading (226).

Shaft assembly (200) further includes a stapling head assembly driver (240) that is slidably received within outer sheath (210). The distal end of stapling head assembly driver (240) is fixedly secured to the proximal end of staple driver member (350). The proximal end of stapling head assembly driver (240) is secured to a drive bracket (250) via a pin (242). It should therefore be understood that staple driver member (350) will translate longitudinally relative to outer sheath (210) in response to translation of stapling head assembly driver (240) and drive bracket (250) relative to outer sheath (210). Stapling head assembly driver (240) is configured to flex such that stapling head assembly driver (240) may follow along the preformed curve in shaft assembly (200) as stapling head assembly driver (240) is translated longitudinally relative to outer sheath (210). However, stapling head assembly driver (240) has sufficient column strength to transfer distal forces from drive bracket (250) to staple driver member (350).

B. Exemplary User Input Features of Circular Stapling Instrument

As shown in FIG. 1, handle assembly (100) includes a pistol grip (112) and several components that are operable to actuate anvil (400) and stapling head assembly (300). In particular, handle assembly (100) includes knob (130), a safety trigger (140) a firing trigger (150), a motor (160), and a motor activation module (180). Knob (130) is coupled with trocar actuation rod (220) via a nut (not shown), such that coarse helical threading (224) will selectively engage a thread engagement feature within the interior of the nut; and such that fine helical threading (226) will selectively engage a thread engagement feature within the interior of knob (130). These complementary structures are configured such that trocar actuation rod (220) will first translate proximally at a relatively slow rate, then translate proximally at a relatively fast rate, in response to rotation of knob (130).

It should be understood that when anvil (400) is coupled with trocar (330), rotation of knob (130) will provide corresponding translation of anvil relative to stapling head assembly (300). It should also be understood that knob (130) may be rotated in a first angular direction (e.g., clockwise) to retract anvil (400) toward stapling head assembly (300); and in a second angular direction (e.g., counterclockwise) to advance anvil (500) away from stapling head assembly (300). Knob (130) may thus be used to adjust the gap distance between opposing surfaces (412, 322) of anvil (400) and stapling head assembly (300) until a suitable gap distance has been achieved.

In the present example, handle assembly (100) comprises a user feedback feature (114) that is configured to provide the operator with visual feedback indicating the positioning of anvil (400) in relation to stapling assembly (300). The operator may thus observe user feedback feature (114) while rotating knob (130), to confirm whether the suitable gap distance between anvil (400) and stapling assembly (300) has been achieved.

Firing trigger (150) is operable to activate motor (160) to thereby actuate stapling head assembly (300). Safety trigger (140) is operable to selectively block actuation of firing trigger (150) based on the longitudinal position of anvil (400) in relation to stapling head assembly (300). Handle assembly (100) also includes components that are operable to selectively lock out both triggers (140, 150) based on the position of anvil (400) relative to stapling head assembly (300). When triggers (140, 150) are locked out, firing trigger (150) is prevented from initiating actuation of stapling head assembly (300). Thus, trigger (150) is only operable to initiate actuation of stapling head assembly (300) when the position of anvil (400) relative to stapling head assembly (300) is within a predefined range.

In the present example, firing trigger (150) of the present example includes an integral actuation paddle, such as the paddle shown and described in U.S. patent application Ser. No. 14/751,231, entitled "Surgical Stapler with Reversible Motor," filed Jun. 26, 2015, the disclosure of which is incorporated by reference herein. The paddle is configured to actuate a switch of motor activation module (180) (FIG. 1) when firing trigger (150) is pivoted to a fired position. Motor activation module (180) is in communication with battery pack (120) and motor (160), such that motor activation module (180) is configured to provide activation of motor (160) with electrical power from battery pack (120) in response to the paddle actuating the switch of motor activation module (180). Thus, motor (160) will be activated when firing trigger (150) is pivoted. This activation of motor (160) will actuate stapling head assembly (300) as described in greater detail below.

Battery pack (120) is operable to provide electrical power to a motor (160) as noted above. Battery pack (120) may be removably coupled with handle assembly (100) through a snap fit or in any other suitable fashion. It should be understood that battery pack (120) and handle assembly (100) may have complementary electrical contacts, pins and sockets, and/or other features that provide paths for electrical communication from battery pack (120) to electrically powered components in handle assembly (100) when battery pack (120) is coupled with handle assembly (100). It should also be understood that, in some versions, battery pack (120) is unitarily incorporated within handle assembly (100) such that battery back (120) cannot be removed from handle assembly (100). Battery pack (120) can include a power source (122). Power source (122) can include a battery, such as a disposable or rechargeable lithium battery and the like.

C. Exemplary Illumination Systems for Circular Stapling Instrument

One aspect of the present disclosure is to provide a mechanism to make surgical stapler (10) more easily located and/or oriented within the patient during a procedure. In certain implementations, it is also an aspect of the present disclosure to identify, via these illumination mechanisms, a separation between the proximal portions of the stapler (i.e., the handle portion) and the distal portions (i.e., the anvil portion). A mechanism for doing so in the present disclosure includes providing one or more illumination systems for the stapler. The illumination systems can include either a single light source or plurality of light sources. These light sources may project in-line with surgical stapler (10) (i.e., longitudinally), as well as radially or at another angle relative to the device's use. Additionally, surgical stapler (10) may use coloration in its illumination systems to additionally provide secondary indicators of orientation or location. For illustration only and not limitation, this can include indicators such as using one color (e.g., red) to indicate the top of the device, and another color (e.g., blue) to indicate the bottom of the device. These lights could additionally then be utilized, with their coloration, to indicate device status. For example, illumination systems can be used to indicate when trocar (330) has been attached to anvil (400). Clinically, this is relevant as a surgical stapler (10) may be held by someone other than the physician, but the end effector assembly (e.g., stapling head assembly (300) and anvil (400)) may be in view of a laparoscopic camera for the surgeon (who cannot see the lens of surgical stapler (10)). Reference will now be made to the various example illumination systems described in the figures.

FIGS. 1 and 4-6 in particular provide views of different illumination systems that can be used within a surgical stapler (10). In one example, and referring specifically to FIG. 4 for illustration, head (334) of trocar (330) can include trocar light (602). Trocar light (602) can be positioned distally on head (334) so that the location of trocar (330) is clearly visible as trocar (330) is inserted into bore (422) of shank (420). Trocar light (602) can be positioned on the very distal tip of head (334), or alternatively trocar light (602) can be positioned on one or more sides of trocar (330) near the distal tip of head (334) so as to project the light from trocar light (602) radially, as shown in FIG. 4. Any of the lights described herein, including without limitation trocar light (602), radial staple lights (604), distal staple light (608), and longitudinal rows of lights (606), (610), and anvil light (612) can include light emitting diodes (LEDs), laser diodes (LDs), and the like. One implementation includes lights that have sufficient intensity to be seen through patient tissue during a procedure.

It is also contemplated that the entire distal end of trocar (602) can be illuminated, and as such trocar light (602) could be the entire distal end of trocar (330). In these examples, the distal end of trocar (330) can be made of a clear material (e.g., a plastic) that acts as a light pipe. The tip of trocar (330) then illuminates as described herein. In certain implementations, when the illumination of trocar (330) is completely covered that indicates anvil (400) is in place and presumed connected. In alternative or additional implementation, trocar light (602) can shine through the distal end of anvil (400). Anvil (400) can include a distal cap (808) (see illustrated in FIGS. 1 and 7C). This cap (808) can be made of a translucent/light dispersing material, and below cap (808) can be a direct path into lumen (422) of shank (420). As such, when trocar (330) is inserted into lumen (422) of shank (420), and anvil light (612) is illuminated, the light therefrom can pass through the translucent or transparent distal cap (808). This can provide an indication that trocar (330) is fully seated into anvil (400).

FIG. 4 also shows an alternative or additional embodiment wherein stapling head assembly (300) includes a plurality of radial staple lights (604) extending around a perimeter of tubular casing (310). The radial placement of radial staple lights (604) provide an easy reference for the location of stapling head assembly (300) in the human body. Surgical stapler (10) can include many radial staple lights (604) around the perimeter of tubular casing (310) as shown so as to ensure the distal end of stapling head assembly (300) is visible from any direction in the patient. In other embodiments, a fewer quantity of radial staple lights (604) can be used than what is shown in FIG. 4, including the quantities as shown in the example of FIG. 1.

In some examples, stapling head assembly (300) includes one or more longitudinal rows of lights (606), (610) positioned on a surface of tubular casing (310) and extending parallel to longitudinal axis (600) of stapling head assembly (300). A first longitudinal row of lights (606) can extend along the surface of surface of tubular casing (310). In some examples, first longitudinal row of lights (606) can extend from one of radial staple lights (604) extending around a perimeter of tubular casing (310). This later example provides a stapling head assembly (300) that both indicates a location of the distal end of stapling head assembly (300) (e.g., via radial staple lights (604) extending around the distal perimeter) and orientation of stapling head assembly (300) (e.g., via looking at the angle of the first longitudinal row of lights (606) within the patient). In some examples, stapling head assembly (300) can include second longitudinal row of lights (610) that can be substantially similar to first longitudinal row of lights (606). Second longitudinal row of lights (610) can be used to provide an orientational indicator at a different side of stapling head assembly (300). First longitudinal row of lights (606) and second longitudinal row of lights (610) can be collectively referred to herein as one or more longitudinal rows of lights (606), (610). The one or more longitudinal rows of lights (606), (610) can be substantially parallel to each other, as shown in FIG. 4.

Stapling head assembly (300) can alternatively, or additionally, include a plurality of distal staple lights (608) positioned around deck surface (322), and distal staple lights (608) can indicate a location of deck surface (322) during operation of the apparatus. Instead of projecting radially like the one or more longitudinal rows of lights (606), (610) and radial staple lights (604), distal staple lights (608) project parallel to the longitudinal axis (600) of stapling head assembly (300). As such, distal staple lights (608) provide a reference for the tissue that will be transected by surgical stapler (10). Distal staple lights (608) can be evenly spaced radially around deck surface (322) and proximate staple openings (324).

Figure 8A:
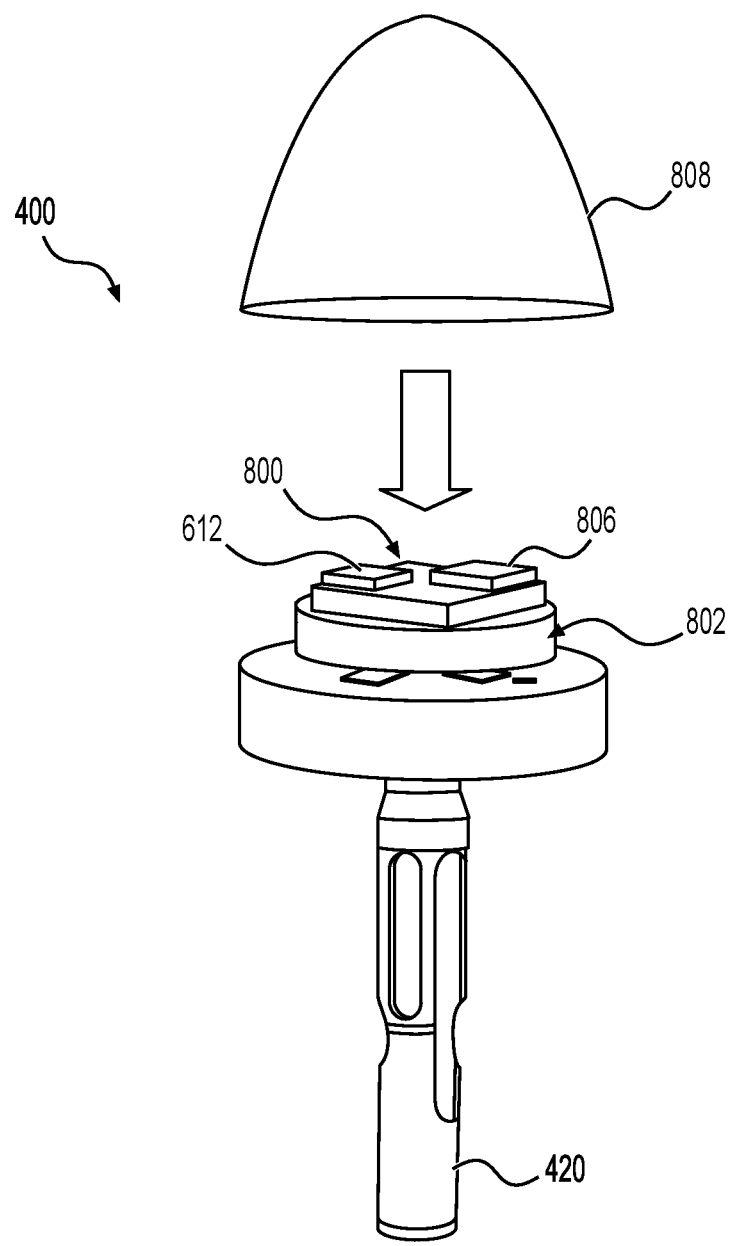
FIG. 8A depicts an anvil with an anvil circuit board.
Figure 8B:
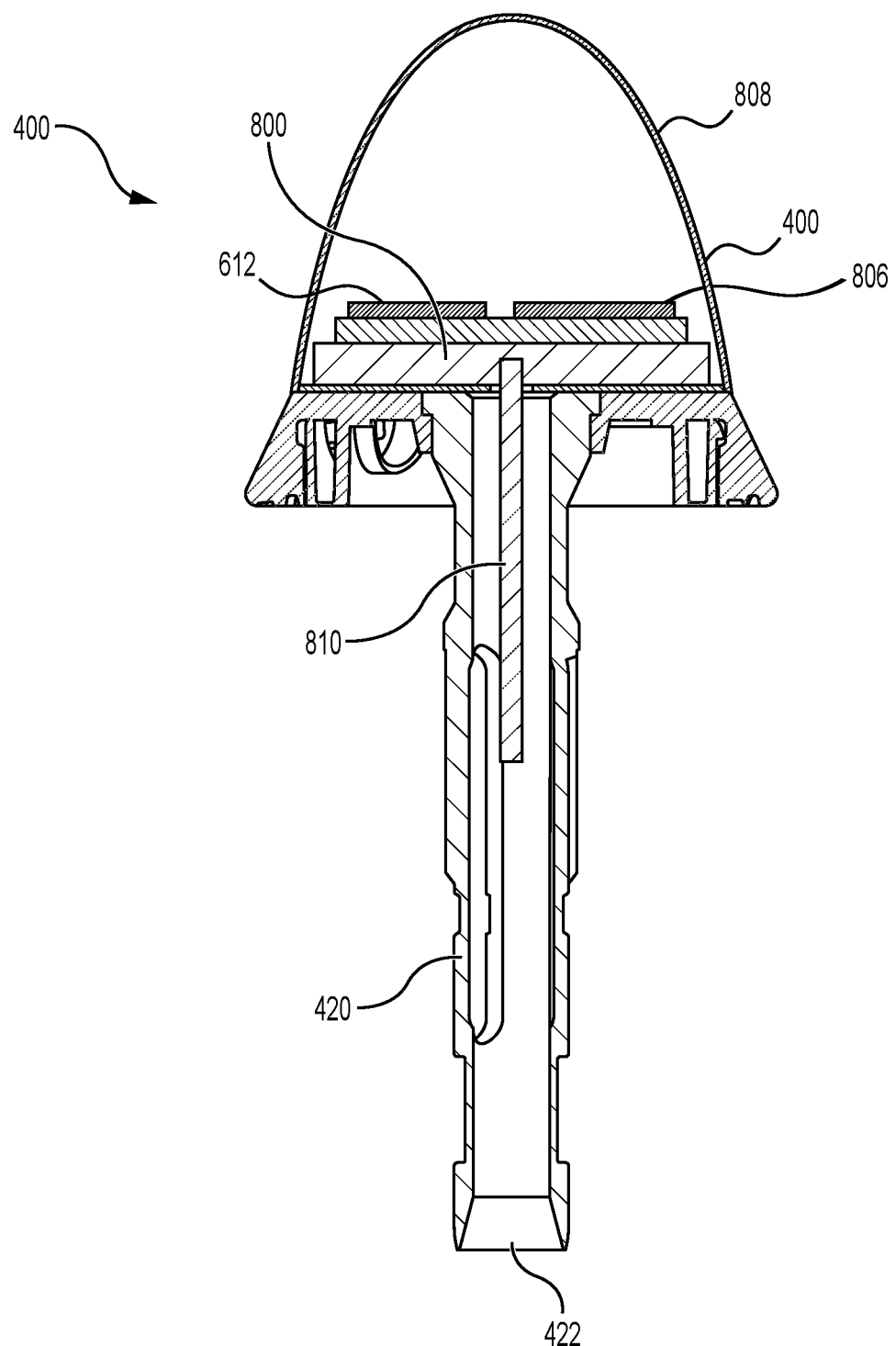
FIG. 8B shows a cross-sectional view of the anvil of FIG. 8A.

In one embodiment, surgical stapler (10) can include a smart (i.e., non-passive) anvil (400), in that anvil (400) can include electronic components in addition to the aforementioned mechanical components. As such, anvil (400) can include anvil light (612) (see FIG. 1). Anvil light (612) can be positioned at the distal end of anvil (400); alternatively, or additionally, anvil light (612) can be placed around the side surfaces of anvil (400) so as to project light radially. In some examples, anvil (400) can include a self-contained power source, such as a battery, that can power anvil light (612). Alternatively, or additionally, anvil light (612) can be powered by power source (122). In this example, an electrical connection between anvil light (612) and power source (122) can be made in response to trocar (330) contacting shank (420) of anvil (400). This can also provide a means to enable anvil light (612) to change from one state to another in response to trocar (330) being properly positioned into shank (420) of anvil (400). This change and state can include changes of color and/or light pulse frequency, as will be described below. FIGS. 8A and 8B below provide additional information related designs for anvil light (612).

As described above, any of the illumination systems herein can use coloration to provide indications of surgical stapler (10) positioning within the patient. For example, in one example, coloration can indicate which part of surgical stapler (10) at which the operator is looking. For example, first longitudinal row of lights (606) can be positioned at a top of surgical stapler (10) and have a first colored light (e.g., red), and second longitudinal row of lights (610) can be positioned at a bottom of surgical stapler (10) and have a second colored light (e.g., blue). In other examples, the one or more lights can change states in response to a status change of the device. For example, and as described above, any of the lights described herein can change in response to trocar (330) being attached to anvil (400). In response, any of the lights can change from one state to another. To change the state of the lights, stapling head assembly (300) can include switch (702) (see FIGS. 7C and 7D). Surgical stapler (10) can further include controller (704) (see FIG. 1), which can be configured to detect actuation of switch (702) and output a signal to one or more of the aforementioned lights to change their status from a first state to a second state. To illustrate, activation of switch (702) can cause controller (704) to output a signal to first longitudinal row of lights (606) to change first longitudinal row of lights (606) from a first state to a second state. This status can include, for example, changing from one color to another. So, for instance, first longitudinal row of lights (606) can illuminate with red light in an initial configuration, and once trocar (330) is engaged with anvil (400), first longitudinal row of lights (606) can illuminate with green light. Alternatively, or additionally, the change from a first state to a second state can include changing a rate of flashing of the lights. So, for instance, first longitudinal row of lights (606) can pulse at a first, slower frequency in an initial configuration, and once trocar is engaged with anvil (400), first longitudinal row of lights (606) can pulse at a second, faster frequency (or vice versa). Similar changes of state can occur to any of the other lights described herein (e.g., anvil light (612) can change from one color to another once anvil (400) is connected to trocar (330)).

Switch (702) can be engageable by trocar (330). Referring to FIG. 7C to illustrate, switch (702) can be positioned inside stapling head assembly (300). Switch (702) can be activated by trocar (330) moving to a predetermined position. In FIGS. 7C and 7D, this predetermined position is when trocar (330) is retracted to a predetermined position, allowing switch (702) to extend and actuate. In other examples, switch (702) can be positioned on trocar (330) such that switch (702) actuates in response to trocar (330) being positioned inside of bore (422). Switch (702) can be a mechanical switch, or in other examples, switch (702) can be an electrical and/or conductive switch that can actuate in response to the metallic material of trocar (330) contacting the metallic material of shank (420) of anvil (400). Controller (704) can include one or more processors and memory (i.e., one or more non-transitory computer-readable medium) with instructions that can be executed by the one or more processors to cause surgical stapler (10) to perform one or more functions described herein.

D. Exemplary Anastomosis Procedure with Circular Stapling Instrument

FIGS. 7A-7E show surgical stapler (10) being used to form an anastomosis (70) between two tubular anatomical structures (20, 40). By way of example only, the tubular anatomical structures (20, 40) may comprise sections of a patient's esophagus, sections of a patient's colon, other sections of the patient's digestive tract, or any other tubular anatomical structures. In some versions, one or more diseased portions of a patient's colon are removed, with the tubular anatomical structures (20, 40) of FIGS. 7A-7E representing the remaining severed portions of the colon.

Figure 7A:
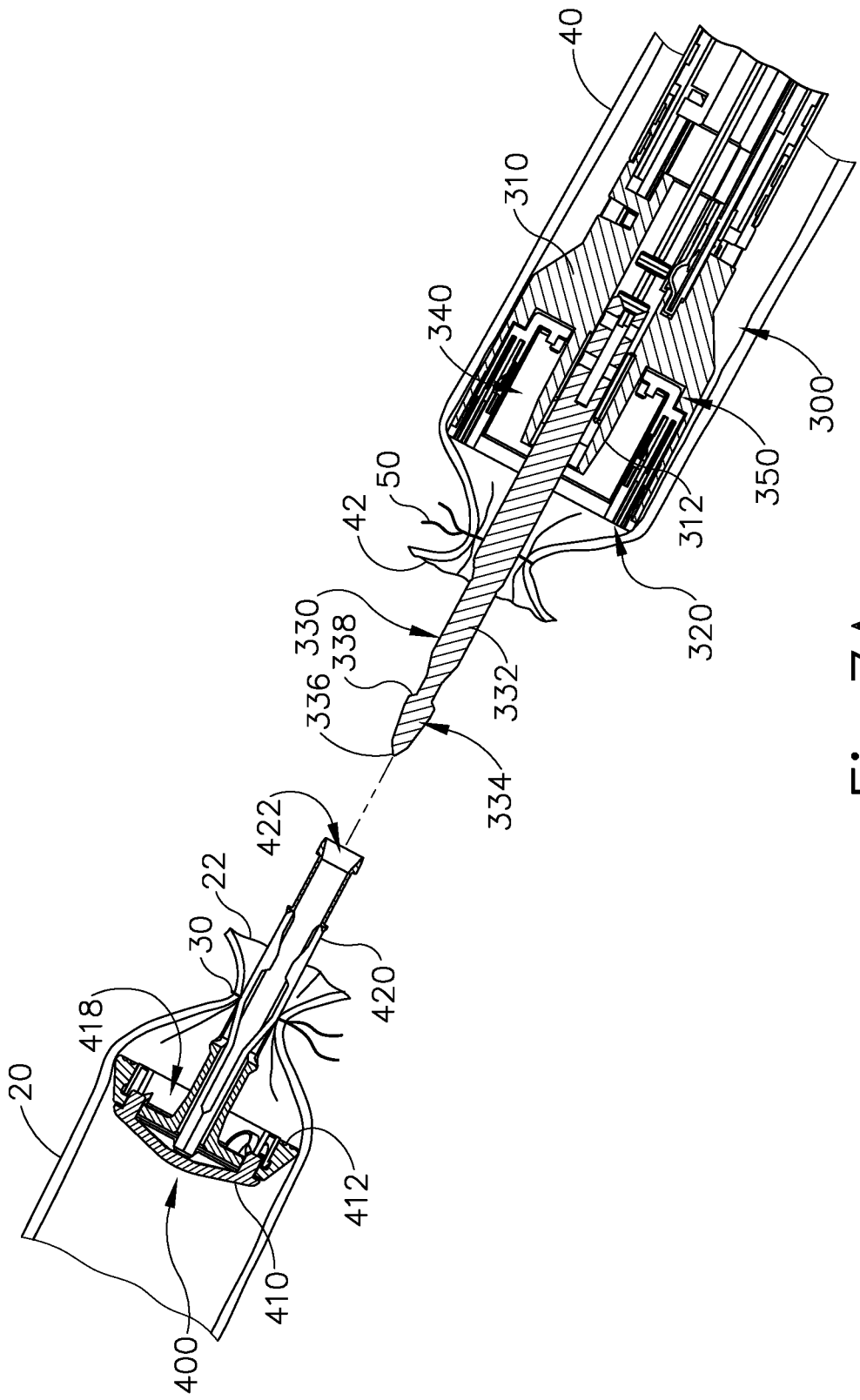
FIG. 7A depicts a cross-sectional side view of the anvil of FIG. 3 positioned within a first section of a digestive tract and the stapling head assembly of FIG. 4 positioned in a second section of the digestive tract, with the anvil separated from the stapling head assembly.

As shown in FIG. 7A, anvil (400) is positioned in one tubular anatomical structure (20) and stapling head assembly (300) is positioned in another tubular anatomical structure (40). In versions where tubular anatomical structures (20, 40) comprise sections of a patient's colon, stapling head assembly (300) may be inserted via the patient's rectum. It should also be understood that the procedure depicted in FIGS. 7A-7E is an open surgical procedure, though the procedure may instead be performed laparoscopically. By way of example only, the surgical procedure may be performed laparoscopically. Various other suitable ways in which surgical stapler (10) may be used to form an anastomosis (70) in a laparoscopic procedure will be apparent to those of ordinary skill in the art in view of the teachings herein.

As shown in FIG. 7A, anvil (400) is positioned in tubular anatomical structure (20) such that shank (420) protrudes from the open severed end (22) of tubular anatomical structure (20). A purse-string suture (30) is provided about a mid-region of shank (420) to generally secure the position of anvil (400) in tubular anatomical structure (20). Similarly, stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40).

Figure 7B:
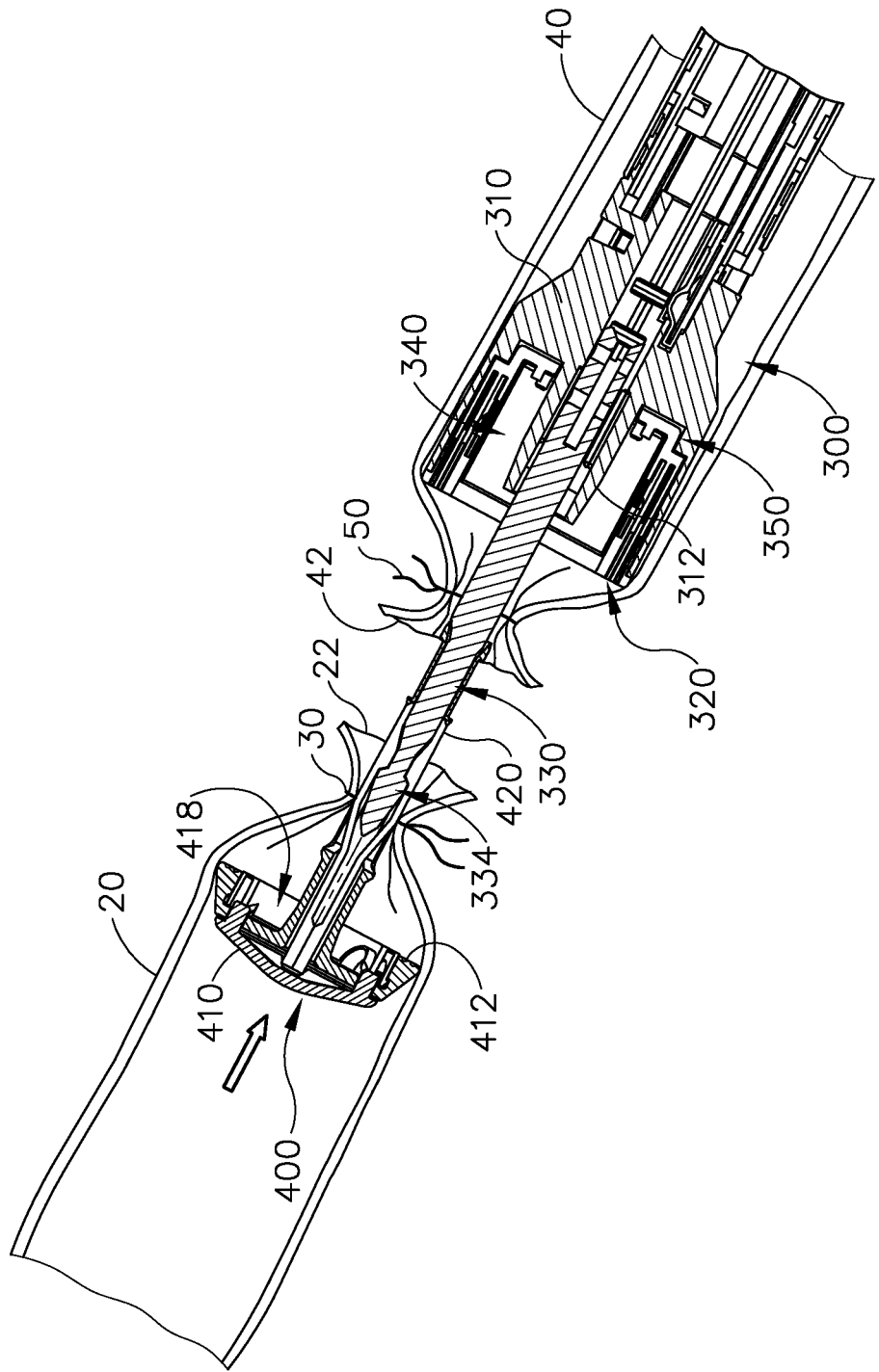
FIG. 7B depicts a cross-sectional side view of the anvil of FIG. 3 positioned within the first section of the digestive tract and the stapling head assembly of FIG. 4 positioned in the second section of the digestive tract, with the anvil secured to the stapling head assembly.
Figure 7C:
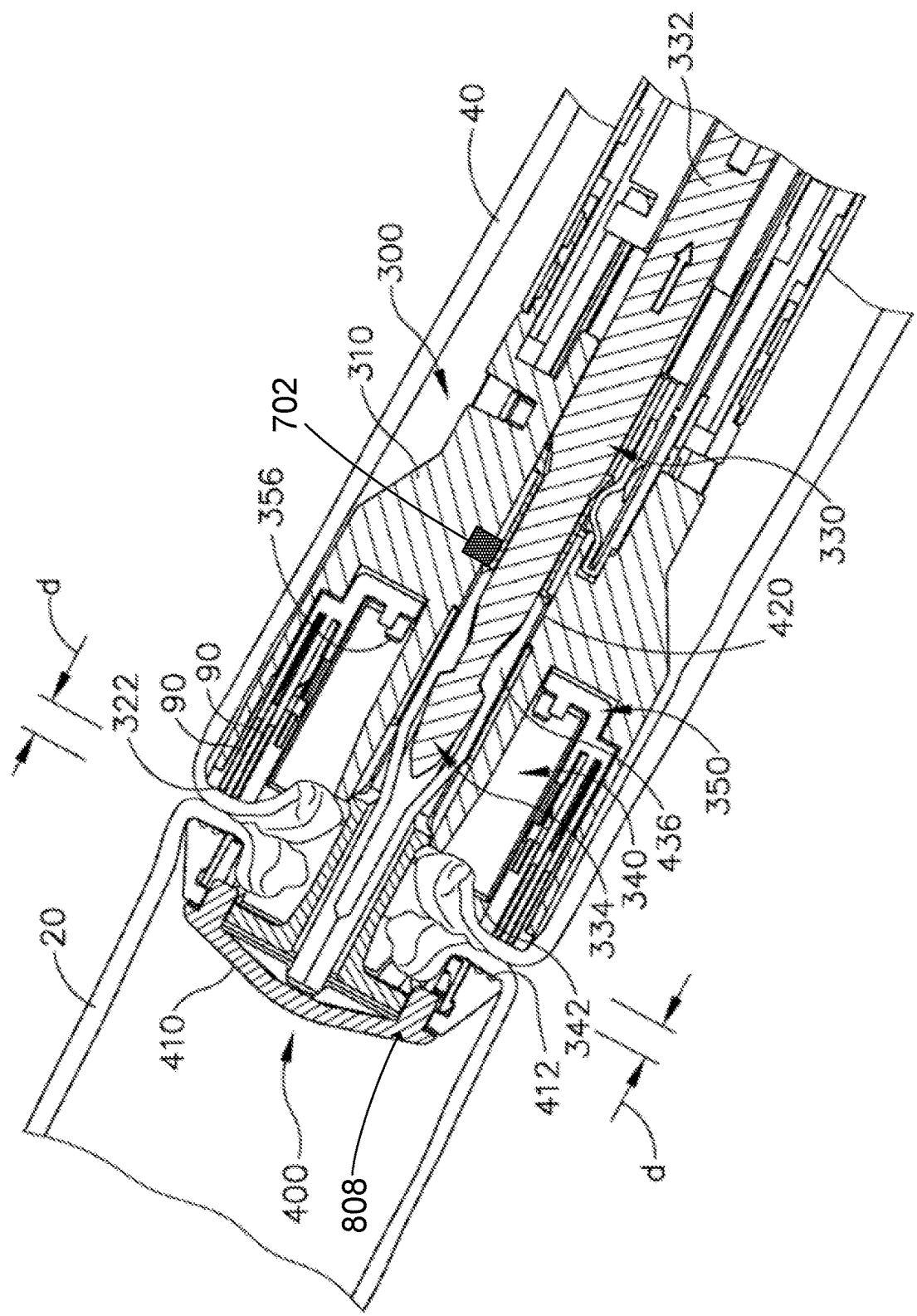
FIG. 7C depicts a cross-sectional side view of the anvil of FIG. 3 positioned within the first section of the digestive tract and the stapling head assembly of FIG. 4 positioned in the second section of the digestive tract, with the anvil retracted toward the stapling head assembly to thereby clamp tissue between the anvil and the stapling head assembly.
Figure 7D:
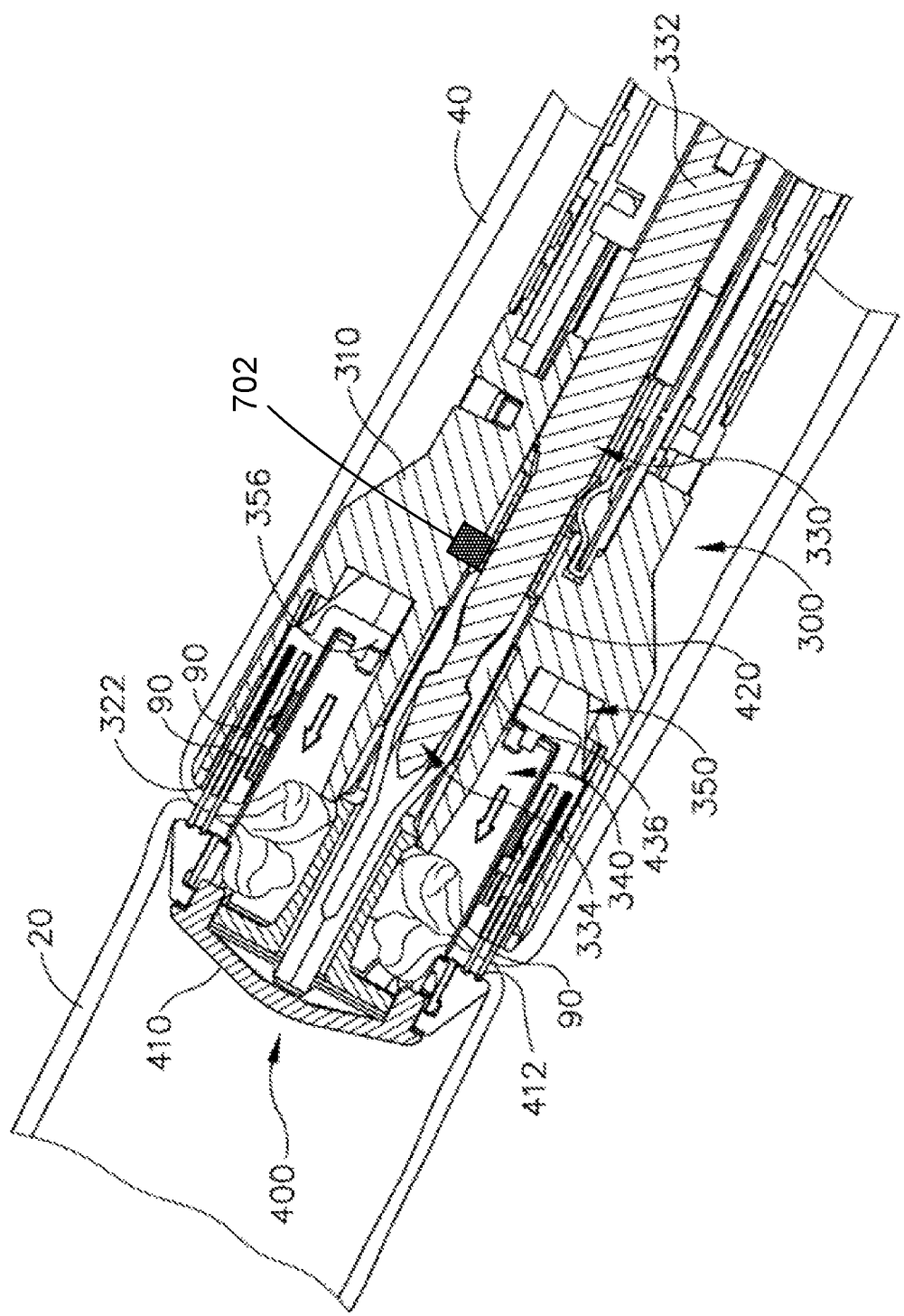
FIG. 7D depicts a cross-sectional side view of the anvil of FIG. 3 positioned within the first section of the digestive tract and the stapling head assembly of FIG. 4 positioned in the second section of the digestive tract, with the stapling head assembly actuated to sever and staple the clamped tissue.

Next, anvil (400) is secured to trocar (330) by inserting trocar (330) into bore (422) as shown in FIG. 7B. Latch members (430) engage head (334) of trocar (330), thereby providing a secure fit between anvil (400) and trocar (330). The operator then rotates knob (130) while holding handle assembly (100) stationary via pistol grip (112). This rotation of knob (130) causes trocar (330) and anvil (400) to retract proximally, as described above. As shown in FIG. 7C, this proximal retraction of trocar (330) and anvil (400) compresses the tissue of tubular anatomical structures (20, 40) between surfaces (412, 322) of anvil (400) and stapling head assembly (300). The operator observes user feedback feature (114) to determine whether the gap distance (d) between opposing surfaces (412, 322) of anvil (400) and stapling head assembly (300) is appropriate; and makes any necessary adjustments via knob (130).

Once the operator has appropriately set the gap distance (d) via knob (130), the operator actuates safety trigger (140) to enable actuation of firing trigger (150). The operator then actuates firing trigger (150). This actuation of firing trigger (150) in turn actuates a switch of motor activation module (180), which in turn activates motor (160) to thereby actuate stapling head assembly (300) by driving knife member (340) and staple driver member (350) distally as shown in FIG. 7D. As knife member (340) translates distally, cutting edge (342) of knife member (340) cooperates with inner edge (416) of anvil (400), thereby shearing excess tissue that is positioned within annular recess (418) of anvil (400) and the interior of knife member (340).

As shown in FIG. 4, anvil (400) of the present example includes a breakable washer (417) within annular recess (418). This washer (417) is broken by knife member (340) when knife member (340) completes a full distal range of motion from the position shown in FIG. 7C to the position shown in FIG. 7D. The drive mechanism for knife member (340) may provide an increasing mechanical advantage as knife member (340) reaches the end of its distal movement, thereby providing greater force by which to break washer (417). Of course, breakable washer (417) may be omitted entirely in some versions. In versions where washer (417) is included, it should be understood that washer (417) may also serve as a cutting board for knife member (340) to assist in cutting of tissue. Such a cutting technique may be employed in addition to or in lieu of the above-noted shearing action between inner edge (416) and cutting edge (342).

As staple driver member (350) translates distally from the position shown in FIG. 7C to the position shown in FIG. 7D, staple driver member (350) drives staples (90) through the tissue of tubular anatomical structures (20, 40) and into staple forming pockets (414) of anvil (400). Staple forming pockets (414) deform the driven staples (90) into a "B" shape as is known in the art. The formed staples (90) thus secure the ends of tissue together, thereby coupling tubular anatomical structure (20) with tubular anatomical structure (40).

Figure 7E:
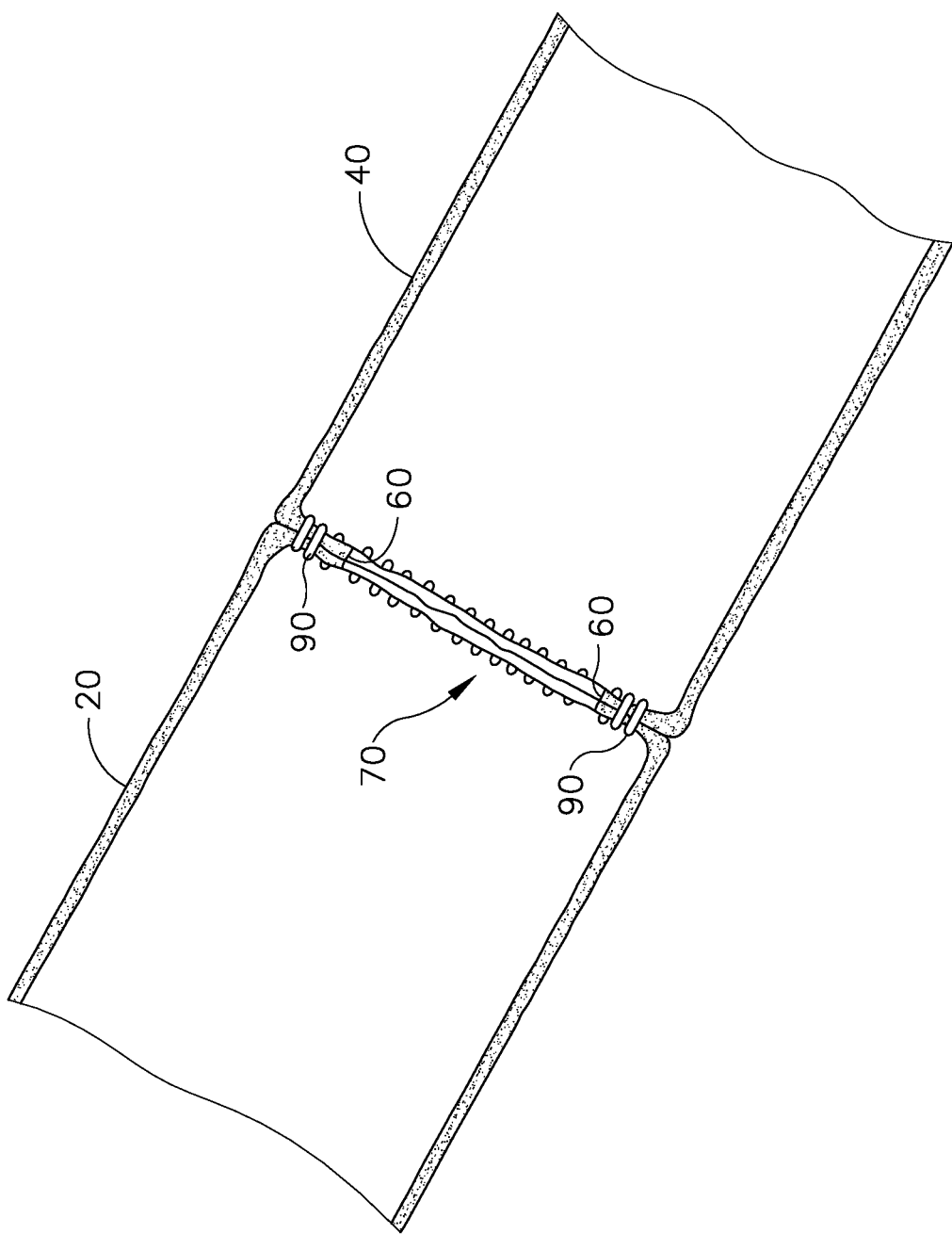
FIG. 7E depicts a cross-sectional side view of the first and second sections of the digestive tract of FIG. 7A joined together at an end-to-end anastomosis.

After the operator has actuated stapling head assembly (300) as shown in FIG. 7D, the operator rotates knob (130) to drive anvil (400) distally away from stapling head assembly (300), increasing the gap distance (d) to facilitate release of the tissue between surfaces (412, 322). The operator then removes surgical stapler (10) from the patient, with anvil (400) still secured to trocar (330). Referring back to the example where the tubular anatomical structures (20, 40) comprise sections of a patient's colon, surgical stapler (10) may be removed via the patient's rectum. With surgical stapler (10) removed, the tubular anatomical structures (20, 40) are left secured together by two annular arrays of staples (90) at an anastomosis (70) as shown in FIG. 7E. The inner diameter of the anastomosis (70) is defined by the severed edge (60) left by knife member (340). Additional information about circular staplers can be found in U.S. Publication No. 2018/0132849, entitled Staple Forming Pocket Configurations For Circular Surgical Stapler Anvil, which is incorporated herein by reference in its entirety.

FIG. 8A depicts an anvil (400) with an anvil circuit board (800), and FIG. 8B shows a cross-sectional view of the anvil (400) of FIG. 8A. As described above, anvil (400) can include anvil light (612) (see also FIG. 1). Anvil light (612) can be positioned at the distal end of anvil (400) as is shown in FIG. 1, and FIGS. 8A and 8B show an alternative to anvil light (612) wherein the light is disposed inside of, internal to, or below a cap (808). Anvil (400) can include components that made anvil (400) a "smart" component of circular stapler (10). As such, anvil (400) can be an integrated component that can operate separately from handle assembly (100), which can be beneficial since anvil (400) is detachably attachable with respect to head assembly (300). Anvil (400) therefore includes power source (802), anvil light (612), and switch (806) (switch described below), each of which are positioned on anvil circuit board (800). It will be appreciated that anvil circuit board (800) can also include a memory and processor. The electrical components of anvil circuit board (800) can be sealed within with cap (808). Power source (802) can be a battery, such as a disposable or rechargeable lithium battery and the like. Power source (802) can also be a capacitor-based circuit that can be charged before use by, for example, using the power source 122 (see FIG. 1) or an external charging pod. For example, trocar (330) can charge or activate power source (802) when trocar (330) contacts shank (420).

Anvil light (612) of FIGS. 8A and 8B can be used to indicate placement of anvil (400). In one example, when trocar (330) is inserted into the lumen (422) of the anvil shank (420), the trocar (330) actuates/activates an activator (810) in connection with the switch (806). Actuation or activation of the activator (810) can cause switch (806) to actuate and therefore change the state of the anvil light (612). The change in state can be similar to any of the other examples described herein, including changes to the color or flashing speed of the light emitted from anvil light (612). It is contemplated, as shown in FIG. 8B, that the activator (810) is a rod extending into the lumen (422) of the anvil shank (420). Other types of activators (810) can be used, for example an inductive or hall effect switch. As will be appreciated, if anvil light (612) is positioned inside or under anvil cap (808), anvil cap (808) can be made of a translucent/light dispersing material.

The technology described herein can further be implemented by any of the following numbered clauses:

Clause 1: An apparatus comprising: (A) a trocar (330); (B) a stapling head assembly (300) comprising: a deck surface (322); a tubular casing (310); an array of staple openings (324) formed through the deck surface (322); a plurality of staples (90) associated with the array of staple openings (324), wherein the stapling head assembly (300) is operable to drive the staples (90) through the array of staple openings (324); and a first longitudinal row of lights (606) positioned on a surface of the tubular casing (310) and extending parallel to a longitudinal axis (600) of the stapling head assembly (300); and (C) an anvil (400) comprising: an anvil surface (412) configured to compress tissue against the deck surface (322), wherein the anvil surface (412) defines an array of staple forming pockets (414); and an anvil shank (420) extending along an anvil longitudinal axis, wherein the anvil shank (420) is configured to couple with one of the stapling head assembly (300) and the trocar (330).

Clause 2: The apparatus of Clause 1, wherein the trocar (330) comprises a head (334) and a trocar light (602) positioned proximate the head (334).

Clause 3: The apparatus of Clause 1 or Clause 2 further comprising a controller (704), and wherein: the stapling head assembly (300) comprises a switch (702); and the controller (704) is configured to detect actuation of the switch (702) by the trocar (330) and output a signal to the first longitudinal row of lights (606) to change the first longitudinal row of lights (606) from a first state to a second state.

Clause 4: The apparatus of Clause 3, wherein the first state is a first flashing speed of the first longitudinal row of lights (606), and the second state is a second flashing speed of the first longitudinal row of lights (606), wherein the first flashing speed is different than the second flashing speed.

Clause 5: The apparatus of Clause 3, wherein the first longitudinal row of lights (606) are a first color in the first state, and the first longitudinal row of lights (606) are a second color in the second state, wherein the first color and the second color are different colors.

Clause 6: The apparatus of any of the preceding Clauses, wherein the stapling head assembly (300) further comprises a second longitudinal row of lights (610) positioned on the surface of the tubular casing (310) and extending parallel to the longitudinal axis (600) of the stapling head assembly (300).

Clause 7: The apparatus of Clause 6, wherein the first longitudinal row of lights (606) are a third color, and the second longitudinal row of lights (610) are a fourth color, wherein the third color and the fourth color are different colors.

Clause 8: The apparatus of any of the preceding Clauses, wherein the stapling head assembly (300) further comprises a plurality of radial staple lights (604) extending around a perimeter of the tubular casing (310).

Clause 9: The apparatus of any of the preceding Clauses, wherein the stapling head assembly (300) further comprises a plurality of distal staple lights (608) positioned around the deck surface (322) indicating a location of the deck surface (322) during operation of the apparatus.

Clause 10: The apparatus of any of the preceding Clauses further comprising a power source (122) in electrical communication with the first longitudinal row of lights (606).

Clause 11: An apparatus comprising: (A) a trocar (330); (B) a stapling head assembly (300) comprising: a deck surface (322); a tubular casing (310); an array of staple openings (324) formed through the deck surface (322); a plurality of staples (90) associated with the array of staple openings (324), wherein the stapling head assembly (300) is operable to drive the staples (90) through the array of staple openings (324); and a plurality of distal staple lights (608) positioned around the deck surface (322) indicating a location of the deck surface (322) during operation of the apparatus; and (C) an anvil (400) comprising: an anvil surface (412) configured to compress tissue against the deck surface (322), wherein the anvil surface (412) defines an array of staple forming pockets (414); and an anvil shank (420) extending along a longitudinal axis, wherein the anvil shank (420) is configured to couple with one of the stapling head assembly (300) and the trocar (330).

Clause 12: The apparatus of Clause 11, wherein the trocar (330) comprises a head (334) and a trocar light (602) positioned proximate the head (334).

Clause 13: The apparatus of Clause 11 or Clause 12 further comprising a controller (704), and wherein: the stapling head assembly (300) comprises a switch (702); and the controller (704) is configured to detect actuation of the switch (702) by the trocar (330) and output a signal to the plurality of distal staple lights (608) to change the plurality of distal staple lights (608) from a first state to a second state.

Clause 14: The apparatus of Clause 13, wherein the first state is a first flashing speed of the plurality of distal staple lights (608), and the second state is a second flashing speed of the plurality of distal staple lights (608), wherein the first flashing speed is different than the second flashing speed.

Clause 15: The apparatus of Clause 13, wherein the plurality of distal staple lights (608) is a first color in the first state, and the plurality of distal staple lights (608) is a second color in the second state, wherein the first color and the second color are different colors.

Clause 16: The apparatus of any one of Clauses 11 to 15, wherein the stapling head assembly (300) further comprises a plurality of radial staple lights (604) extending around a perimeter of the tubular casing (310).

Clause 17: The apparatus of any one of Clauses 11 to 16, wherein the stapling head assembly (300) comprises a first longitudinal row of lights (606) positioned on a surface of the tubular casing (310) and extending parallel to the longitudinal axis (600) of the stapling head assembly (300).

Clause 18: The apparatus of Clause 17, wherein the stapling head assembly (300) comprises a second longitudinal row of lights (610) positioned on the surface of the tubular casing (310) and extending parallel to the longitudinal axis (600) of the stapling head assembly (300).

Clause 19: The apparatus of any one of Clauses 11 to 18, wherein the plurality of distal staple lights (608) extend around a perimeter of the deck surface (322) proximate the array of staple openings (324).

Clause 20: An apparatus comprising: (A) a trocar (330); (B) a stapling head assembly (300) comprising: a deck surface (322); a tubular casing (310); an array of staple openings (324) formed through the deck surface (322); a plurality of staples (90) associated with the array of staple openings (324), wherein the stapling head assembly (300) is operable to drive the staples (90) through the array of staple openings (324); a distal staple light (608) positioned around the deck surface (322) indicating a location of the deck surface (322) during operation of the apparatus; and a plurality of radial staple lights (604) extending around a perimeter of the tubular casing (310); and (C) an anvil (400) comprising: an anvil surface (412) configured to compress tissue against the deck surface (322), wherein the anvil surface (412) defines an array of staple forming pockets (414); and an anvil shank (420) extending along a longitudinal axis, wherein the anvil shank (420) is configured to couple with one of the stapling head assembly (300) and the trocar (330).

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometric s, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

The invention is not necessarily limited to the examples described, which can be varied in construction and detail. The terms "distal" and "proximal" are used throughout the preceding description and are meant to refer to a positions and directions relative to the physician or user holding surgical stapler 10. As such, "distal" or "distally" refer to a position distant to or a direction away from the person gripping surgical stapler 10. Similarly, "proximal" or "proximally" refer to a position near or a direction towards the person grasping pistol grip 112 (i.e., toward an operator of surgical stapler 10). Furthermore, the singular forms "a," "an," and "the" include plural referents unless the context clearly dictates otherwise. Furthermore, the use of "couple", "coupled", or similar phrases should not be construed as being limited to a certain number of components or a particular order of components unless the context clearly dictates otherwise.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g., "about 90%" may refer to the range of values from 80.001% to 99.999%.

In describing example embodiments, terminology has been resorted to for the sake of clarity. As a result, not all possible combinations have been listed, and such variants are often apparent to those of skill in the art and are intended to be within the scope of the claims which follow. It is intended that each term contemplates its broadest meaning as understood by those skilled in the art and includes all technical equivalents that operate in a similar manner to accomplish a similar purpose without departing from the scope and spirit of the invention. It is also to be understood that the mention of one or more steps of a method does not preclude the presence of additional method steps or intervening method steps between those steps expressly identified. Similarly, some steps of a method can be performed in a different order than those described herein without departing from the scope of the disclosed technology.

The invention claimed is:

1. An apparatus comprising:
(A) a trocar;
(B) a stapling head assembly comprising:
a deck surface;
a tubular casing;
an array of staple openings formed through the deck surface;
a plurality of staples associated with the array of staple openings, wherein the stapling head assembly is operable to drive the staples through the array of staple openings; and
a first longitudinal row of lights positioned on a surface of the tubular casing and extending parallel to a longitudinal axis of the stapling head assembly; and
(C) an anvil comprising:
an anvil surface configured to compress tissue against the deck surface, wherein the anvil surface defines an array of staple forming pockets; and
an anvil shank extending along an anvil longitudinal axis, wherein the anvil shank is configured to couple with one of the stapling head assembly and the trocar.

2. The apparatus of claim 1, wherein the trocar comprises a head and a trocar light positioned proximate the head.

3. The apparatus of claim 1 further comprising a controller, and wherein:
the stapling head assembly comprises a switch; and
the controller is configured to detect actuation of the switch by the trocar and output a signal to the first longitudinal row of lights to change the first longitudinal row of lights from a first state to a second state.

4. The apparatus of claim 3, wherein the first state is a first flashing speed of the first longitudinal row of lights, and the second state is a second flashing speed of the first longitudinal row of lights, wherein the first flashing speed is different than the second flashing speed.

5. The apparatus of claim 3, wherein the first longitudinal row of lights are a first color in the first state, and the first longitudinal row of lights are a second color in the second state, wherein the first color and the second color are different colors.

6. The apparatus of claim 1, wherein the stapling head assembly further comprises a second longitudinal row of lights positioned on the surface of the tubular casing and extending parallel to the longitudinal axis of the stapling head assembly.

7. The apparatus of claim 6, wherein the first longitudinal row of lights are a third color, and the second longitudinal row of lights are a fourth color, wherein the third color and the fourth color are different colors.

8. The apparatus of claim 1, wherein the stapling head assembly further comprises a plurality of radial staple lights extending around a perimeter of the tubular casing.

9. The apparatus of claim 1, wherein the stapling head assembly further comprises a plurality of distal staple lights positioned around the deck surface indicating a location of the deck surface during operation of the apparatus.

10. The apparatus of claim 1 further comprising a power source in electrical communication with the first longitudinal row of lights.

11. An apparatus comprising:
(A) a trocar;
(B) a stapling head assembly comprising:
a deck surface;
a tubular casing;
an array of staple openings formed through the deck surface;
a plurality of staples associated with the array of staple openings, wherein the stapling head assembly is operable to drive the staples through the array of staple openings; and
a plurality of distal staple lights positioned around the deck surface indicating a location of the deck surface during operation of the apparatus; and
(C) an anvil comprising:
an anvil surface configured to compress tissue against the deck surface, wherein the anvil surface defines an array of staple forming pockets; and
an anvil shank extending along a longitudinal axis, wherein the anvil shank is configured to couple with one of the stapling head assembly and the trocar.

12. The apparatus of claim 11, wherein the trocar comprises a head and a trocar light positioned proximate the head.

13. The apparatus of claim 11 further comprising a controller, and wherein:
   the stapling bead assembly comprises a switch; and
   the controller is configured to detect actuation of the switch by the trocar and output a signal to the plurality of distal staple lights to change the plurality of distal staple lights from a first state to a second state.

14. The apparatus of claim 13, wherein the first state is a first flashing speed of the plurality of distal staple lights, and the second state is a second flashing speed of the plurality of distal staple lights, wherein the first flashing speed is different than the second flashing speed.

15. The apparatus of claim 13, wherein the plurality of distal staple lights is a first color in the first state, and the plurality of distal staple lights is a second color in the second state, wherein the first color and the second color are different colors.

16. The apparatus of claim 11, wherein the stapling head assembly further comprises a plurality of radial staple lights extending around a perimeter of the tubular casing.

17. The apparatus of claim 11, wherein the stapling head assembly comprises a first longitudinal row of lights positioned on a surface of the tubular casing and extending parallel to the longitudinal axis of the stapling head assembly.

18. The apparatus of claim 17, wherein the stapling head assembly comprises a second longitudinal row of lights positioned on the surface of the tubular casing and extending parallel to the longitudinal axis of the stapling head assembly.

19. The apparatus of claim 11, wherein the plurality of distal staple lights extend around a perimeter of the deck surface proximate the array of staple openings.

20. An apparatus comprising:
   (A) a trocar;
   (B) a stapling head assembly comprising:
      a deck surface;
      a tubular casing;
      an array of staple openings formed through the deck surface;
      a plurality of staples associated with the array of staple openings, wherein the stapling head assembly is operable to drive the staples through the array of staple openings;
      a distal staple light positioned around the deck surface indicating a location of the deck surface during operation of the apparatus; and
      a plurality of radial staple lights extending around a perimeter of the tubular casing; and
   (C) an anvil comprising:
      an anvil surface configured to compress tissue against the deck surface, wherein the anvil surface defines an array of staple forming pockets; and
      an anvil shank extending along a longitudinal axis, wherein the anvil shank is configured to couple with one of the stapling head assembly and the trocar.

* * * * *